United States Patent [19]

Kinsolving et al.

[11] Patent Number: 4,486,601
[45] Date of Patent: Dec. 4, 1984

[54] ESTERS OF 2-ADAMANTANONE OXIME

[75] Inventors: C. Richard Kinsolving, Fairport; Vassil St. Georgiev, Rochester, both of N.Y.

[73] Assignee: Pennwalt Corporation, Philadelphia, Pa.

[21] Appl. No.: 524,484

[22] Filed: Aug. 19, 1983

[51] Int. Cl.$^3$ .......................................... C07C 131/02
[52] U.S. Cl. .................................................. 564/254
[58] Field of Search ........................................ 564/254

[56] References Cited

U.S. PATENT DOCUMENTS 3,951,950  4/1976  Narayanan et al. ................ 424/274

OTHER PUBLICATIONS

Schenk, C. et al., *Chemical Abstracts*, vol. 94, (1981), #46,371r.

*Primary Examiner*—Natalie Trousof
*Assistant Examiner*—L. Hendriksen

[57] ABSTRACT

Esters of 2-adamantanone oxime are prepared and are disclosed as possessing anti-inflammatory activity and antiviral activity against murine hepatitis virus.

11 Claims, No Drawings

ESTERS OF 2-ADAMANTANONE OXIME

INTRODUCTION AND BACKGROUND

The present invention provides a novel class of 2-adamantanone oxime esters that possess anti-inflammatory activity. While certain imino-2-adamantanes are known (Biochem. Pharmacol 31, 1693, (1982); C.A. 94, 46371r (1981); Ger. 2651083; C.A. 89 129241w, (1978)), one of which was reported to have psychotropic activity, the oxime esters of the present invention have not been reported.

THE INVENTION

The present invention provides a novel class of esters of 2-adamantanone oxime of Formula I below:

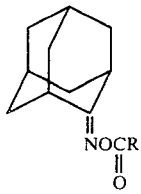

Formula I wherein R represents lower alkyl, lower alkenyl, aryl, aralkyl and aralkenyl wherein the aryl groups may bear substituents for hydrogen, such as, for instance, nitrile, nitro, halo and alkoxy.

The compounds of the present invention can be conveniently prepared by reacting 2-adamantanone oxime with sodium hydride followed by the addition of an appropriate acid chloride.

The following example is cited to illustrate the invention. It is not intended to limit it in any manner.

EXAMPLE 1

0-(Phenylacetyl)-2-Adamantanone Oxime

2-Adamantanone oxime (10.0 g, 0.061 mol) was added to a suspension of sodium hydride (2.93 g, 0.122 mol) in 60 mol tetrahydrofuran and the reaction mixture was refluxed for 5 hours. Then, phenylacetyl chloride (9.43 g, 0.061 mol) was added slowly and the reaction mixture was refluxed for 6 hours. After cooling, chloroform was added and the inorganic precipitate was filtered off. The organic solution was evaporated to dryness leaving a crude oxime ester derivative (9 g) which was recrystallized from cyclohexane, providing purified 0-(phenylacetyl)-2-adamantanone oxime melting between 74° and 80° C.

The technique of Example 1 was employed to prepare a series of related compounds as identified in the Table below using the appropriate acid chloride and a suitable recrystallization solvent (as indicated).

TABLE

| Example | R | mp, °C. | recryst'n. solvent |
|---|---|---|---|
| 2 | CH₃ | 108–110 | iso-PrOH |
| 3 | C₆H₄CN—4 | 144–146 | iso-PrOH |
| 4 | C₆H₄NO₂—4 | 160–161 | iso-PrOH |
| 5 | C₆H₄NO₂—3 | 123–126 | iso-PrOH |
| 6 | CH₂—C₆H₄—Cl | 84–85 | iso-PrOH |
| 7 | CH₂CH₂—C₆H₅ | 70–73 | petr. ether |
| 8 | CH=CHCH₃ | 76–80 | iso-PrOH |
| 9 | CH=CH—C₆H₅ | 129–131 | iso-PrOH |
| 10 | CH=CH—C₆H₄—OCH₃ | 136–139 | iso-PrOH |

The compounds of this invention have displayed biological activity, particularly as anti-inflammatory agents as indicated by results of the Carrageenan-induced rat paw edema assay. In addition, the compound of Example 3 has exhibited antiviral activity against murine hepatitis virus.

Many equivalent modifications of the above invention will become apparent to those skilled in the art without a departure from the inventive concept.

What is claimed is:

1. The compounds

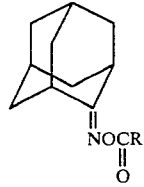

wherein R is a member of the class of lower alky, lower alkenyl, aryl, aralkyl and aralkenyl wherein the aryl groups may bear substituents for hydrogen selected from the group consisting of nitrile, nitro, halo and alkoxy.

2. The compound of claim 1 wherein R is

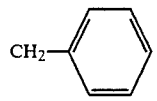

3. The compound of claim 1 wherein R is CH₃.

4. The compound of claim 1 wherein R is C₆H₄CN—4.

5. The compound of claim 1 wherein R is C₆H₄NO₂—4.

6. The compound of claim 1 wherein R is C₆H₄NO₂—3.

7. The compound of claim 1 wherein R is

8. The compound of claim 1 wherein R is
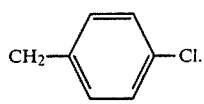
9. The compound of claim 1 wherein R is
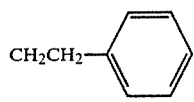
CH=CHCH₃.
10. The compound of claim 1 wherein R is
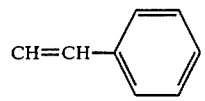
11. The compound of claim 1 wherein R is
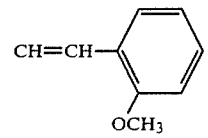
* * * * *